United States Patent [19]

Schindler et al.

[11] 4,253,456
[45] Mar. 3, 1981

[54] ARTIFICIAL ENDOCRINAL GLAND

[75] Inventors: Johannes G. Schindler, Marburg; Wilfred Schäl, Bad Homburg, both of Fed. Rep. of Germany;

[73] Assignee: Dr. Eduard Fresenius Chemisch-pharmazeutisch Industrie KG, Apparatebau KG, Bad Homburg, Fed. Rep. of Germany

[21] Appl. No.: 935,600

[22] Filed: Aug. 21, 1978

[30] Foreign Application Priority Data

Aug. 23, 1977 [DE] Fed. Rep. of Germany ....... 2737922

[51] Int. Cl.³ .............................................. A61M 5/14
[52] U.S. Cl. ............................. 128/214 R; 128/214 E; 128/DIG. 13; 210/321.2
[58] Field of Search ........... 128/213 R, 213 A, 214 R, 128/214 B, 214 E, DIG. 12, DIG. 13, DIG. 3, 632–637; 422/44, 48, 45; 210/321 B, 96.1, 96.2, 22

[56] References Cited

U.S. PATENT DOCUMENTS

| 3,015,331 | 1/1962  | Warrick ................................. 422/45     |
| 3,183,908 | 5/1965  | Collins et al. .......................... 422/45     |
| 3,512,517 | 5/1970  | Kadish et al. ...................... 128/214 R       |
| 3,518,982 | 7/1970  | Timmins et al. ..................... 128/632         |
| 3,838,682 | 10/1974 | Clark et al. .................. 128/214 E X          |
| 4,055,175 | 10/1977 | Clemens et al. ..................... 128/213         |
| 4,060,485 | 11/1977 | Eaton ........................... 210/321 B X        |
| 4,081,372 | 3/1978  | Atkin et al. .................. 128/213 A X          |

FOREIGN PATENT DOCUMENTS

| 2017112 | 10/1971 | Fed. Rep. of Germany ...... 128/213 A |
| 2261247 | 7/1973  | Fed. Rep. of Germany ...... 128/214 R |
| 2152355 | 12/1973 | Fed. Rep. of Germany ...... 128/214 R |
| 2601893 | 7/1976  | Fed. Rep. of Germany ........... 128/632 |
| 232476  | 4/1969  | U.S.S.R. ............... 128/214 E |
| 305410  | 7/1971  | U.S.S.R. ............... 128/632 |
| 435826  | 12/1974 | U.S.S.R. ............... 128/214 E |

*Primary Examiner*—Kyle L. Howell
*Attorney, Agent, or Firm*—Omri M. Behr; Martin Sachs

[57] ABSTRACT

An artificial endocrinal gland comprises a blood dialyzer for transferring a part of the blood to a measuring liquid in a separate circuit, an analyzer for quantatively determining this part and producing in the measuring liquid conversion products compatible to the patient's metabolism, a controller responsive to the analyzer and a device for supplying quantities of hormone to the patient's body under the control of the controller.

11 Claims, 4 Drawing Figures

ARTIFICIAL ENDOCRINAL GLAND

The invention relates to an artificial endocrinal gland. It is particularly suitable for use as an artificial pancreas beta cell, artificial beta cells called "artificial abdominal salivary glands" somewhat imprecisely, are described for example, in (1) A.M. Albisser and others: Clinical Control of Diabetes by the Artificial Pancreas. Diabetes 23 (1974) pp. 397 to 404.

(2) W. Kerner and others: Attempts to Perfect Normalization of Glucose Tolerance Test of Severe Diabetics by Artificial Beta Cell. Horm. Metab Res. 8 (1976), pp. 256 to 261.

(3) E. C. Layne and others: Continuous Extracorporeal Monitering of Animal Blood Using the Glucose Electrode. Diabetes 25 (1976) pp. 81 to 89.

The natural functioning of the beta cells of the endocrinal pancreas consists chiefly in producing and releasing the hormone insulin depending on the content of glucose in the blood in order to control thereby the take up of the nutrients dissolved in the blood into the body cells and more particularly the build up of glycogen from excess glucose present in the blood. If this control mechanism is faulty then, as is known, the illness Diabetes mellitus (or simply diabetes) is caused.

A system which should replace the natural functioning of the beta cells must have three essential components, i.e., (a) a device for measuring the concentration of glucose in the blood, (b) a device for supplying insulin into the bloodstream and (c) a controller which controls the quantity of insulin to be supplied per unit time based on measured values. The system can be extended still further by additionally providing for the supply of a medium (for example glucose) which counteracts the insulin.

In the above-mentioned artificial beta cells described in various pieces of literature, the blood continuously removed from the patient and previously treated to prevent coagulation is passed through a dialyzer in which the glucose molecules diffuse through a membrane into an indicator solution. The change in colour of the indicator caused by this is determined colorimetrically. This principle of measurement requires a large technical expenditure and the equipment necessary is correspondingly large in volume and in weight. As well, considerable consumption of liquid is required so that construction of the equipment in the form of a device portable on the patient's body, which is desirable per se, had previously to be regarded as being outside the bounds of technical possibility. An important problem, chiefly for permanent use remained completely unsolved until now, i.e. the problem of continuous analysis of the content of glucose in the blood without continuous loss of blood.

In the prior art mentioned above at (3) it is proposed to use a glucose electrode instead of the dialyser and color indicator for determining the content of glucose in the blood. A glucose electrode comprises an oxygen sensitive electrode with the enzyme glucose oxidase being arranged in the path to the electrode. In the presence of glucose and oxygen, the glucose oxidase causes catalytic oxidation of the glucose to form gluconic acid and hydrogen peroxide. The concentration of oxygen arising in the region of the electrode and thus the strength of the current flowing through the electrode are controlled according to the quantity of glucose present. These electrodes require little space and are reliable and have a long service life when in a suitable embodiment. It has even been proposed to implant these electrodes into the patient's skin; however this has not proved suitable in the long term. With the glucose electrodes it is possible basically to measure in the whole blood (i.e. without removing the read blood plates beforehand); the result of measurement is influenced by different factors however and is not reliable. Furthermore, when using a glucose electrode as a measuring probe, the problem remains of the constant loss of blood and elimination of waste products.

According to the invention there is provided an artificial endocrinal gland comprising a blood dialyzer for transferring a part of the blood to be monitored, a measuring liquid, an analyzer for quantitatively determining this part, a controller responsive to the analyzer and a device controlled by the controller for supplying hormone to the patient's body, wherein that separate circuits are provided for the blood flowing through the dialyzer and the measuring liquid and wherein conversion products produced by the analyzer and thereafter present in the measuring liquid are compatible to the metabolism of the patient.

This artificial endocrinal gland has the task of reducing the volume and the weight of the artificial gland, particularly an artificial beta cell and at the same time of avoiding the continuous loss of blood by the patient. To this end blood and measuring liquid are passed in separate circuits so that it is unnecessary to make available reservoir containers for the waste products. The precondition for this is that the conversion products of the analyzer in the measuring liquid are compatible to the metabolism of the patient because these conversion products diffuse through the dialysis membrane back into the blood and are supplied to the patient's body. When using a glucose electrode to measure the glucose content, this condition is fulfilled because the gluconic acid formed by conversion with oxygen can take part in the metabolism of the patient.

Since the blood circulation and the measuring liquid circulation are separated by the dialysis membrane, there is a safe barrier to infection between the circulating blood and the remaining parts of the system.

Miniaturization may be carried still further in accordance with a refinement of the invention by constructing the dialyzer as a catheter and by inserting it into the body itself. Thus the entire system can be constructed in the form of a device which can be carried on or in the body of the patient.

The scope of application of the invention is not limited to replacement of the beta cell function of the pancreas but can also be used to replace the functioning of other internal secretory glands, for example in order to control the material exchange of calcium in the case of deficient functioning of the parathyroid gland.

The invention will now be described in greater detail, by way of example, with reference to the drawings in which.

Figure 1:
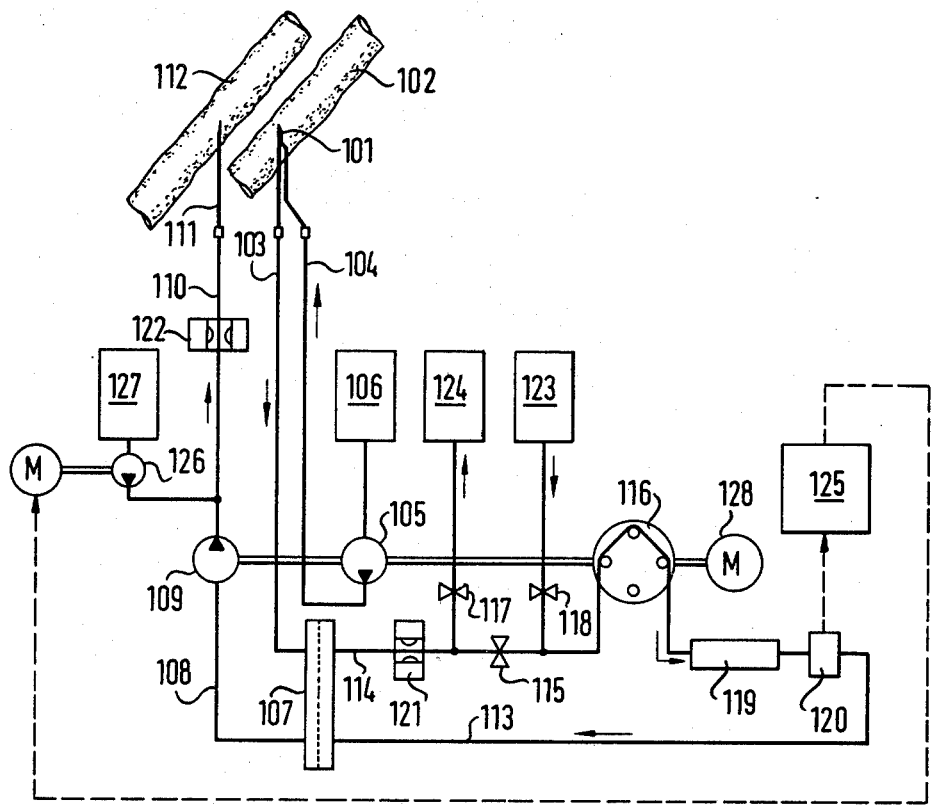
FIG. 1 shows the liquid circuit of a first embodiment of the invention having an extracorporeal dialyzer and the further function elements in schematic view.

With the embodiment shown in FIG. 1 the blood is removed by means of a dual-passage hollow needle 101 of known type which is inserted into a patient's blood vessel 102. These hollow needles have two coaxial liquid channels, the inner one of which is connected to a line 103 and serves to remove the blood, while a solution containing a substance inhibiting coagulation, heparin for example, is pumped from a supply container 106 by a pump 105 through a line 104, and through the outer channel connected thereto. The action of medicaments which inhibit coagulation can, in known manner, be neutralized by suitable antidotes—in the case of heparin this is protamine—before the blood is reintroduced into the body. The function of the inner and outer channels can be exchanged. The flowrate of the heparin solution is substantially smaller than the quantity of blood removed per unit time. It is the purpose of this arrangement to reduce the coagulation characteristics of the blood immediately at the point of removal such that coagulation in the attached system is prevented. The blood flowing through the line 103 reaches a dialyzer 107 which contains a semipermeable membrane for separating the blood and measuring liquid circuits. After the blood has passed the dialyzer it flows through a line 108, a pump 109 and a line 110 attached thereto back to the patient. The actual return takes place through a hollow needle 111 which is introduced into a blood vessel 112. The pump 109, which conveys a certain quantity of blood per unit time through the dialyzer, can be inserted in the supply line 103 of the dialyzer instead of in the outlet line.

While the blood flows along one surface of the semipermeable membrane of the dialyzer, a measuring liquid is passed along the other surface and circulates in the attached analysis circuit. The liquid being supplied to the dialyzer through a line 113 takes on approximately the same glucose concentration on its path along the membrane surface as the blood flowing on the opposite surface of the membrane, since the membrane has a high permeability for glucose because of the relatively low molecule size of the glucose so that rapid balancing out of the concentrations can take place. The measuring liquid flows out through a line 114 and, saturated with the glucose content of the blood, reaches a pump 116 through a hose constricting valve 115 which is open in normal operation. Hose constriction valves 117 and 118 are in these circumstances closed. The pump 116 is used at the same time as an oxygenator i.e., the liquid conveyed by it is saturated at the same time up to the oxygen content of the surrounding atmosphere. Details of the operation of the oxygenator pump 116 are explained further below.

The liquid, saturated with oxygen up to the oxygen partial pressure of the air, passes through an enzyme reactor 119 after the pump 116. The enzyme reactor is provided with the enzyme glucose oxidase, which converts glucose into gluconic acid while consuming oxygen. The enzyme reactor contains the enzyme, preferably in immobilized form, e.g. bonded at the surface of a polymeric carrier material. One of several known embodiments of these reactors comprises, for example, a simple hose which carries the enzyme on its inner surface. The partial pressure of oxygen at the outlet of the reactor, a measure of the glucose concentration, is measured by an oxygen-sensitive probe 120. After passing the measuring probe 120, the liquid is passed through the line 113 back to the dialyzer and passes through the described circuit again. The circulating liquid accepts approximately the composition of the blood because of the properties of the dialyzer 107 with respect to its low molecular weight components, so that the final products of the glucose conversion catalyzed by glucose oxidase can be further processed by the patient's metabolism. On the other hand there is the possibility of inserting several measuring probes, e.g., in the form of ion-selective and/or gas-sensitive electrodes into the analysis circuit, possibly including other enzymatic reactions, if other analysis values are to be obtained for other purposes.

Since the semi-permeable membrane serves as a germ-proof barrier between the circulating blood and the measuring circuit, it is desirable to recognize a leakage in this membrane in good time. A membrane leakage detector 121 in the form of a light barrier, comprising a light source and a light sensor services for this purpose and the line 114, constructed as a transparent hose, passes through it. With a leakage in the membrane, blood passes into the circulating liquid so that the light intensity picked up by the light sensor is reduced and the entire circulation can be stopped by safety arrangements provided in the control of the system. A similar safety arrangement in the form of a light barrier 122 serves to sense the pressure of air in the blood supplied back to the patient. In the case of air leakage into the system, air can be sucked by the pump 109 and conveyed into the line leading to the patient. In order to eliminate any danger to the patient which might occur as a result, provision is made in the control of the system for the pump 109 or the entire circulation to be stopped automatically when an increased light intensity occurs at the light sensor of the light barrier 122, indicating the presence of air.

In order to monitor and maintain the measurement accuracy, provision is made to control and calibrate the measuring device formed by the elements 116, 119 and 120 at regular time intervals. To carry this out, the hose constricting valve 115 is closed, and the hose constricting valves 117 and 118 are opened. As a result a calibrating liquid having defined glucose concentration is supplied to the analysis path from a supply vessel 123. The same quantity of liquid flows through the hose constricting valve 117 into the collecting container 124. It is advisable to add bacteriostatically or bacteriocidally acting substances or fungicides to the calibration liquid which is located in the supply vessel 123 in order to suppress growth of germs in the analysis circuit.

The oxygen measuring probe is connected to an electronic controller 125, the purpose of which consists essentially in controlling an infusion pump for insulin in dependence on the measured concentration of glucose. This infusion pump 126, which can be constructed for example as a hose pump, conveys a solution containing insulin from a supply vessel 127 into the line 110 leading to the patient so that the insulin reaches the blood circulation of the patient together with the returned blood.

The electronic controller should take into account both the actual value of the glucose concentration $K_G$ and its time differential quotient $dK_G/dt$ i.e., the rate of change of the glucose concentration, whereby the rate of change is evaluated by a non-linear function f so that a "probable final value" of the glucose concentration arises as a calculation magnitude in the form: $K_{GE} = K_G + f(dK_G/dt)$. A second non-linear evaluation function determines the quantity of insulin $(m_I)$ to be supplied per unit time depending on the "probable final value" of the glucose concentration, i.e., $m_I = g(K_{GE})$.

Suitable evaluation functions are known from literature on the subject. In order to take into account automatically the control values determined during the periodically implemented calibration checks with respect to possible changes in sensitivity of the measuring device, the controller must moreover be in a position to provide the measured value $K_G$ with an appropriate correction factor determined during calibration. The described computation operations which must be carried out by the control 125 can be implemented in various ways. Of course, because of the complexity of the entire task, it is obviously suitable to use a digital system with a microprocessor for this purpose.

A discontinuous mode of operation is provided in a preferred refinement of the controller in the form that calculation of the optimum quantity of insulin and accordingly the dosage and supply of this quantity takes place with the aid of the insulin pump only at fairly large time intervals, for example at the end of an interval of time of 10 to 20 minutes in each case. For this, the actual values of the glucose concentration and its rate of change are determined as average values over a part of the time interval. As a result, there is the possibility of interposing a calibration process into each of these time intervals or at least after a certain number (for example 5 or 10) time intervals have passed; in each case a calibration process is provided during the next time interval.

From FIG. 1 it may be seen that a common drive in the form of an electric motor 128 can be used for the pumps 109, 105 and 116, which are driven essentially at a constant speed. Different gearing ratios which may be necessary have not been shown in FIG. 1. Besides this simplification achieved by the common drive, there is another simplification owing to the fact that the motor 128 can also be used to control the individual measuring and calibration processes and the functions of the controller 125 connected therewith, whereby actuation of the hose constricting valves 115, 117 and 118 for the calibration process is instigated by the drive motor 128. This may be achieved advantageously by providing a motor controller cams (not shown) controlled via a suitable reduction gearing, these cams actuating corresponding contact elements for triggering the electrical functions of the controller 125 and operating drive levers for closing and opening the hose constricting valves 115, 117 and 118.

Figure 2:
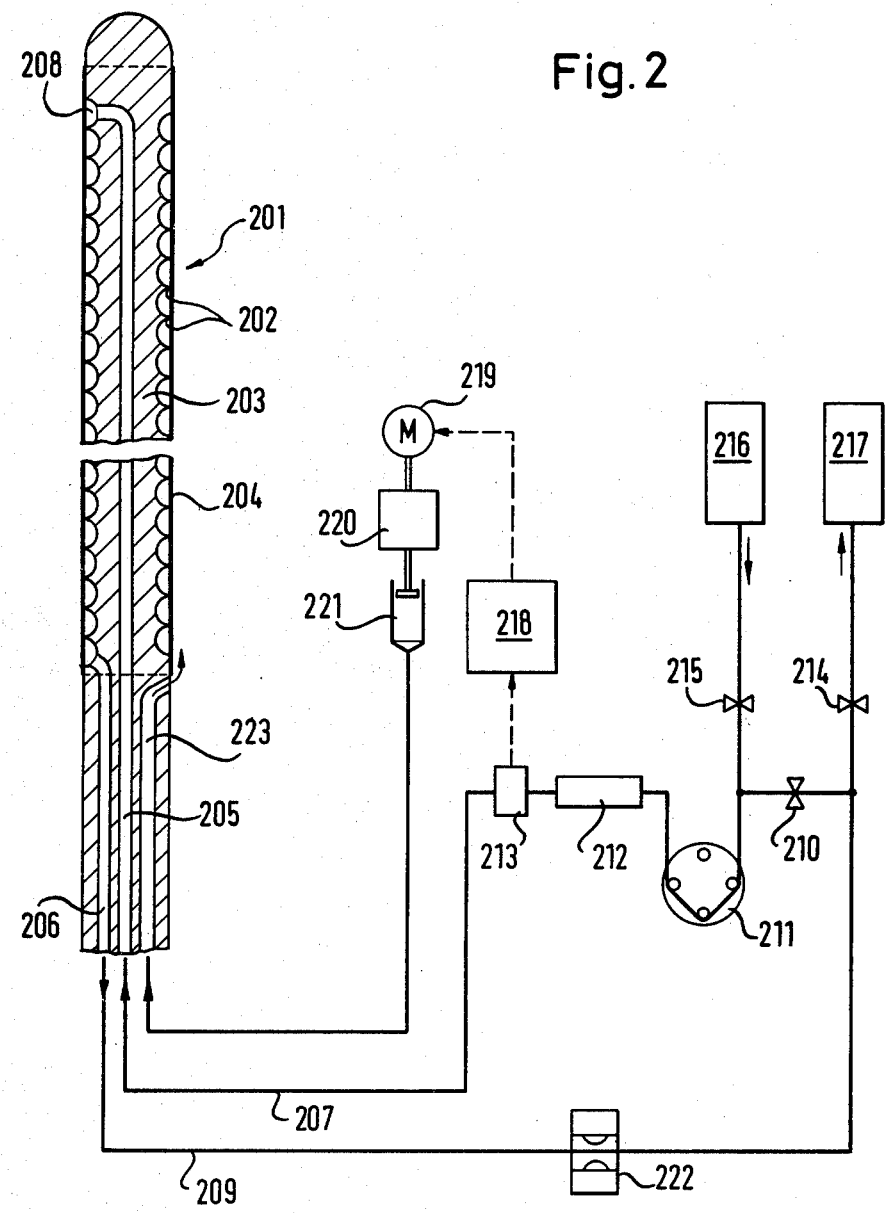
FIG. 2 shows the liquid circuit of a second embodiment in schematic view including a schematic partial sectional view of the dialysis catheter used.

A second embodiment of the liquid circuit of an "artificial pancreas beta cell" is shown in FIG. 2. This example represents a device which can be carried on the patient's body. The difference with respect to the first embodiment consists essentially in that an intracorporeal dialyzer in the form of a dialysis or filter catheter is provided instead of the extracorporeal dialyzer. The dialysis catheter 201 is inserted into one of the patient's blood vessels and has a dialysis membrane 204 supported on ribs 202 of a base element 203 running helically or in parallel to the longitudinal axis and supply and outlet channels 205 and 206. It forms a part of the analysis circuit for measuring the glucose concentration. The liquid, which enters the channel 205 through a line 207 and is passed at 208 to the rear side of the membrane, takes on approximately the same concentration of glucose as the blood flowing at the outer membrane surface. The liquid flowing out through a line 209 and saturated up to the glucose content of the blood reaches a pump oxygenator 211 through a hose constricting valve 210 which is open in normal operation. After passing an enzyme reactor 212 and an oxygen measuring probe 213, the liquid is passed back through the line 207 into the channel 205 of the catheter and passes through the described circuit again. The functions of these elements are the same as in the first embodiment. The hose constricting valves 214 and 215 as well as the containers 216 and 217 serve similarly for calibration. Here too it is advisable to mix germ growth prevention substances with the calibrating liquid contained in the container 216 so that these substances pass into the analysis circuit during the periodic calibration. Similarly, the addition of substances inhibiting coagulation, such as heparin may be advantageous in order to suppress the coagulation tendency of the blood at the outer surface of the membrane.

An insulin infusion pump controlled by an electronic controller 218 can be constructed as a hose pump or, as shown in this example, as an injection pump comprising a motor 219, a linkage mechanism 220 and an injection nozzle 221 which contains the insulin. The linkage mechanism 220 converts the rotary movement of the motor 219 into a linear motion for driving the piston of the injection nozzle 221; the latter is connected to a channel 223 of the catheter 201, which channel opens freely at the surface of the catheter.

For automatically recognizing a possible defect in the membrane of the catheter, a membrane leakage detector in the form of a light barrier 222 is provided as in the first embodiment through which the line 209, constructed as a transparent hose, passes. The reduction in the light intensity at the light sensor caused by the appearance of blood in this line triggers a signal which stops the drive of the pump 211 and, moreover, initiates an acoustic fault alarm.

Figure 3:
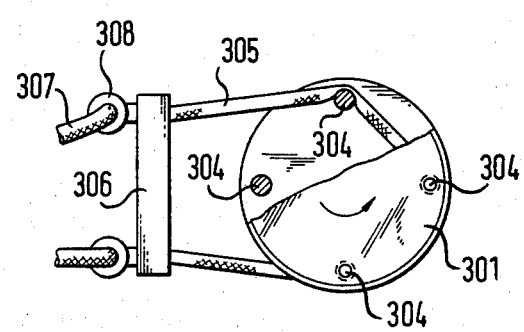
FIG. 3 shows a schematic side view of the pump oxygenator used in both embodiments.
Figure 4:
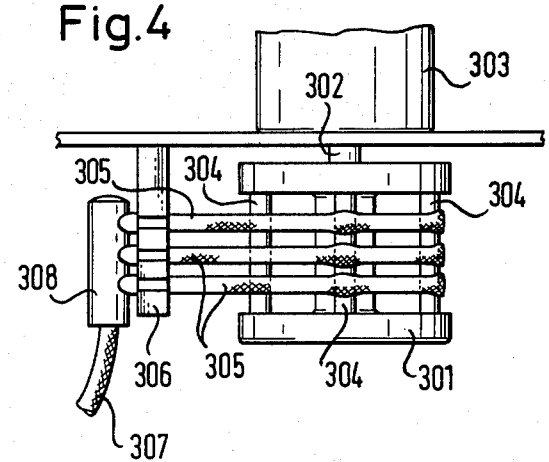
FIG. 4 shows a plan view of the pump of FIG. 3.

An embodiment of the pump oxygenator 116 or 211 mentioned is shown in FIGS. 3 and 4. This device, which unites the functions of a pump and an oxygenator, is similar in its construction to a normal hose pump, preferably in the form of a so-called statorless hose pump, in which the pump hose is looped at a certain prestress over the rotor so that the cross-section of the hose is completely closed at the points of abutment on the rollers of the rotor as a result of this prestressing. The fact that certain plastics, for example silicone rubber, which are suitable as a material for hoses of hose pumps because of their resilience, have a very high permeability to gas is utilized for the simultaneous function of the pump as an oxygenator. It has been shown that if suitably dimensioned, a very active operation as an oxygenator can be achieved besides the pump action. To this end, the smallest possible wall thickness and a large surface area of the hose and a relatively long residence time of the medium in the pump are advantageous. Optimization with respect to differing requirements is to be achieved by branching the conveyed flow into several parallel partial flows and by dividing them into several parallel pump hoses.

In the embodiment shown in FIGS. 3 and 4, the rotor 301 which is set in rotation by the axle 302 of a geared motor 303, carries four rollers 304 which are mounted on the rotor so as to be freely rotatable. Pump hoses 305 are tensioned over these rollers, their ends being fixed in a mounting 306. Distributor elements 308 serve to distribute the medium flowing in the line 307 to the pump hoses.

In the embodiments described in conjunction with FIG. 1 and FIG. 2, the possibility known per se of counter regulation by means of infusion of glucose (or possibly glucagon) in the case of a drop below a certain glucose concentration in the blood was dispensed with in the interests of the most extensive simplification possible in terms of apparatus, since a deficit of glucose can also be cancelled out by means of oral administration of glucose. However, the described systems can be improved by the provision of a display device connected to the oxygen-measuring probe 120 or 213, from which the actual glucose concentration can be read off and/or a device for monitoring a limit value can be provided, which device triggers a warning signal when certain critical values of the glucose concentration are reached.

The invention is not limited to use as a replacement for the beta function of the pancreas, as described in detail, but can also serve for substitution in the case of failure of other endocrine glands. The control of the calcium metabolism in the case of failure of the parathyroid glands may be mentioned as an example. The parathyroid glands are the location where parathormone is formed, this hormone increasing the calcium ion activity in the blood and in the extracellular liquid. The antidote to the parathormone is the thyrocalcitonin which is formed in the parafollicular cells of the thyroid gland.

In the case of failure of the paratyroid glands, the arrangements according to FIG. 1 or FIG. 2 can be used substantially unchanged. The element 120 or 213 would be constructed as a calcium selective sensor in this case and the enzyme reactor 119 or 212 dispensed with. The supply vessel 123 or 216 would contain a calibrating solution having a defined calcium ion concentration. The vessel 127 or 221 would contain the parathormone. Possibly an additional automatic injection device could be provided for thyrocalcit onin and/or calcium.

The arrangement shown and described provides a substantial increase in medical and technical functional safety since any risk of infection can be avoided and the analysis device cannot be rendered faulty by components of the blood. As a result of automatic periodic testing and calibration of the measuring system, a high functional safety can be achieved. In addition the detectors for membrane leaks and possible air detector contribute to this. The technical expenditure can be kept low if the functions of oxygenator and pump are united in the manner described and if the drive motor of the pump is used simultaneously to actuate the hose constricting valves during calibration and as a timing generator for the measuring and calibration processes.

We claim:

1. A system intended for use in a patient for simulating an endocrinal gland by transferring a component of the flowing blood from said patient being monitored and treated into a measuring fluid flow path, comprising:
    (a) means for providing a constant flow of measuring fluid in a closed path, said measuring fluid not being consumed or diluted during measurement in said measuring fluid flow path;
    (b) dialyzing means coupled to said flowing blood and having a semipermeable membrane, said membrane permitting a component of said blood being monitored to be transferred to said measuring fluid in said measuring fluid flow path;
    (c) reactor means serially disposed in said measuring fluid flow path, said reactor means containing a compound in immobilized form for catalytic conversion of said component of said blood to be transferred to said measuring fluid flow path;
    (d) analyzer means serially coupled in said measuring fluid flow path for quantatatively determining the amount of said component of blood, said analyzer conversion products produced and appearing in said measuring fluid being compatable with the metabolism of said patient;
    (e) means coupled into said blood being monitored for supplying a material into said blood to modify the amount of said component appearing in said blood; and
    (f) controller means responsive to said analyzer means for controlling the quantity of said material supplied by said supplying means.

2. A system for simulating an endocrinal gland according to claim 1 wherein said reactor means comprises an enzyme reactor and said compound for catalytic conversion comprises an enzyme bonded at the surface of a polymeric carrier material.

3. A system for simulating an endocrinal gland according to claim 1 further including a switching means coupled in said measuring fluid flow path for providing periodic calibration of said analyzer means with a calibration liquid while blocking off circulation of said measuring fluid flow path 4. A system for simulating an endocrinal gland according to claim 3, wherein said means for providing a constant circulation of said measuring fluid includes pump means, said pump means being activated by a motor, said motor also controlling said switching means provided in said fluid flow path.

5. A system for simulating an endocrinal gland according to claim 1 further including optical monitoring devices for detecting blood in the measuring fluid and air in the fluid returned into said monitored blood.

6. A system for simulating an endocrinal gland according to claim 5 wherein said gland is a pancreas beta cell and said measuring fluid flow path includes an oxygenator, an enzyme reactor and an oxygen sensitive measuring probe arranged serially in said measuring fluid path.

7. A system for simulating an endocrinal gland according to claim 6 wherein said oxyginator is constructed as a roller pump with hoses for simultaneously permitting the passage of oxygen from the surrounding air into said measuring fluid by mechanical agitation of said hoses and circulating said measuring fluid in said closed measuring fluid flow path.

8. A system intended for use in a patient for simulating an endocrinal gland by transferring a component of the flowing blood from said patient being monitored and treated into a measuring fluid flow path comprising:
    (a) dialyzing means coupled to said flowing blood and having a semipermeable membrane, said membrane permitting a component of said blood being monitored to be transferred to said measuring fluid in said measuring fluid flow path;
    (b) said measuring fluid flow path forming a closed path in which said measuring fluid is recirculating without any consumption of measuring fluid and is blocked off from any additional liquid supplied during measurement,
    said closed measuring path including:
        (i) means for providing a constant circulation of measuring fluid flow,
        (ii) reactor means serially coupled in said measuring fluid flow path, said reactor means containing a compound for catalytic conversion of said blood component to be transferred to said measuring fluid flow path, said compound being in immobilized form, and (iii) analyzer means serially coupled in said measuring fluid flow path for quantitatively determining the amount of said component of said blood within said measuring fluid flow path;

(c) means coupled into said blood being monitored for supplying a material into said blood to modify the amount of said component of said blood being transferred to said measuring fluid flow path; and (d) controller means responsive to said analyzer means for controlling the quantity of said material supplied by said supplying means.

9. A system for simulating an endocrinal gland according to claim 8 wherein said quantitatively determining means includes a catalytic conversion of said component of said blood.

10. A system intended for use in a patient for simulating an endocrinal gland by transferring a component of the flowing blood from said patient being monitored and treated into a measuring fluid flow path comprising:

(a) means for providing a constant flow of measuring fluid in a closed path, said measuring fluid not being consumed or diluted during measurement in said measuring fluid flow path;

(b) dialyzing means coupled to said flowing blood and having a semipermeable membrane, said membrane permitting a component of said blood being monitored to be transferred to said measuring fluid in said measuring fluid flow path;

(c) reactor means serially coupled in said measuring fluid flow path, said reactor means containing a compound in immobilized form for catalytic conversion of said component of said blood to be transferred to said measuring fluid flow path; and (d) analyzer means serially coupled in said measuring fluid flow path for quantitatively determining the amount of said component of blood, said analyzer conversion products produced and appearing in aid meausring fluid being compatible with the metabolism of said patient.

11. A system for simulating an endocrinal gland according to claim 10 further including:

(d) means coupled in said blood being monitored for supplying a material into said blood to modify the amount of said component appearing in said blood; and (e) controller means responsive to said analyzer means for controlling the quantity of said material supplied by said supplying means.

* * * * *